US012805830B2

(12) United States Patent
Harris et al.

(10) Patent No.: US 12,805,830 B2
(45) Date of Patent: Nov. 24, 2026

(54) ULTRASOUND-BASED INTERMITTENT OR CONTINUOUS INTRACRANIAL PRESSURE MONITORING DEVICE AND METHOD

(71) Applicant: The Government of the United States, as represented by The Secretary of the Army, Fort Detrick, MD (US)

(72) Inventors: Tyler Harris, Vass, NC (US); Jason Perez, Midlothian, VA (US)

(73) Assignee: The Government of the United States, as represented by The Secretary of the Army, Fort Detrick (MD)

( * ) Notice: Subject to any disclaimer, the term of this patent is extended or adjusted under 35 U.S.C. 154(b) by 0 days.

(21) Appl. No.: 18/854,331

(22) PCT Filed: Mar. 31, 2023

(86) PCT No.: PCT/US2023/017119
§ 371 (c)(1),
(2) Date: Oct. 4, 2024

(87) PCT Pub. No.: WO2023/196190
PCT Pub. Date: Oct. 12, 2023

(65) Prior Publication Data

US 2025/0261923 A1 Aug. 21, 2025

Related U.S. Application Data

(60) Provisional application No. 63/328,229, filed on Apr. 6, 2022.

(51) Int. Cl.
*A61B 8/08* (2006.01)
*A61B 8/00* (2006.01)

(52) U.S. Cl.
CPC .................. *A61B 8/08* (2013.01); *A61B 8/42* (2013.01); *A61B 8/4236* (2013.01); (Continued)

(58) Field of Classification Search
CPC ........... A61B 8/08; A61B 8/42; A61B 8/4236; A61B 8/4272; A61B 8/4477; A61B 8/461; A61B 8/56
See application file for complete search history.

(56) References Cited

U.S. PATENT DOCUMENTS 8,394,025 B2 3/2013 Ragauskas et al.
8,672,851 B1 * 3/2014 Quirk .................. A61B 8/4218 600/459

(Continued)

OTHER PUBLICATIONS

PCT/US2023/017119 International Search Report and Written Opinion, Jul. 3, 2023.

*Primary Examiner* — Michael J Carey
*Assistant Examiner* — Maria Christina Talty
(74) *Attorney, Agent, or Firm* — Robinson + Cole LLP

(57) ABSTRACT

An apparatus for monitoring Intracranial Pressure (ICP) includes a non-invasive, flexible, wearable device (30), (60) with micro ultrasonic transducer arrays (32) fixed thereon. The wearable device (30), (60) is attached to the closed eyelid (21) of a conscious or unconscious patient with an adhesive (48). Using ultrasound sonography, the ultrasonic transducer arrays (32) on the wearable device (30), (60) image the optic nerve (26) behind the eyeball (20) to measure the Optical Nerve Sheath Diameter (ONSD). The ONSD provides an indication of the ICP in real time.

19 Claims, 5 Drawing Sheets

(52) U.S. Cl.
CPC .......... *A61B 8/4272* (2013.01); *A61B 8/4477* (2013.01); *A61B 8/461* (2013.01); *A61B 8/56* (2013.01)

(56) References Cited

U.S. PATENT DOCUMENTS

| | | | | |
|---|---|---|---|---|
| 8,864,670 | B2 | 10/2014 | Lisiecki et al. | |
| 2007/0093698 | A1 | 4/2007 | Goldberger et al. | |
| 2010/0331684 | A1* | 12/2010 | Ragauskas ............... | A61B 8/06 600/438 |
| 2012/0197118 | A1* | 8/2012 | Lisiecki ................... | A61B 8/04 600/438 |
| 2016/0022246 | A1 | 1/2016 | Ragauskas | |
| 2018/0168544 | A1* | 6/2018 | Davidsen ............. | A61B 8/4254 |
| 2018/0296182 | A1* | 10/2018 | Maltz ..................... | G16H 50/30 |
| 2020/0367774 | A1* | 11/2020 | Hong ................... | A61B 8/4209 |

* cited by examiner

ULTRASOUND-BASED INTERMITTENT OR CONTINUOUS INTRACRANIAL PRESSURE MONITORING DEVICE AND METHOD

STATEMENT OF GOVERNMENT INTEREST

The invention described herein may be manufactured, used and licensed by or for the United States Government.

BACKGROUND OF THE INVENTION

The invention relates to measurements of intracranial pressure and, in particular, to apparatus and methods based on transorbital sonography to measure intracranial pressure.

Elevated Intracranial Pressure (ICP) often occurs from head trauma and can result in stroke, seizures, neurological damage or even death. Rapid diagnosis and monitoring are critical to allow for immediate medical intervention. Diagnosis of dangerously high levels of ICP may be achieved through lumbar puncture, invasive transcranial devices, computed tomography scan or magnetic resonance imaging. Lumbar puncture and invasive transcranial devices are invasive. Computed tomography and magnetic resonance imaging require complex machinery and radiologists. Procedurally placed ICP monitoring devices include a fluid-filled transduced ventriculostomy, a subdural screw, or an epidural sensor. These three procedurally placed ICP monitoring devices require a neurosurgeon and a burr hole through the skull.

Attempts at noninvasive ICP monitoring have been made and include two-depth transorbital Doppler ultrasound, ultrasound time of flight, and transcranial Doppler ultrasonography. These methods require complex permanently-housed machinery, highly-trained technicians and a medical provider who is highly skilled in this type of ultrasound. The current methods for both diagnosis and monitoring are not feasible for use in emergency, combat or patient transport situations.

A simpler non-invasive diagnosis method for measuring ICP has been demonstrated to be effective. This method uses direct ocular measurements of the optic nerve sheath diameter (ONSD). However, a highly-skilled medical provider is required to perform this method and this method cannot be used for continuous monitoring of ICP.

A direct correlation between ONSD and ICP is known. In the context of an ultrasound system, algorithms are known that automate the process of measuring and reporting the ONSD and integrate the process with a portable ultrasound system, without the need to manually measure the ONSD from the ultrasound image of the optical nerve. One example of such an algorithm is disclosed by Gerber, S. et al.; *Automatic Estimation of the Optic Nerve Sheath Diameter from Ultrasound Images; Imaging for Patient-Customized Simulations and Systems for Point-of-Care Ultrasound* (2017); 2017 September; 10549:113-120. doi: 10.1007/978-3-319-67552-7_14; the entirety of which is expressly incorporated by reference herein.

The known portable ultrasound systems use ultrasonic transducer housings that are held by a technician in the vicinity of the eyeball area of the face to measure ONSD. But the hand-held transducers cannot easily be used for continuous monitoring of ICP over time because to do so requires a person to tirelessly hold the hand-held apparatus continuously over the eyeball area of the patient. And, in certain conditions, such as evacuation of a patient by air, land or sea, the instability of the position of the patient or of the evacuation vehicle may make it difficult for the user to hold the transducer housing steady, even intermittently. In addition, there may not be ample space for the user in an evacuation vehicle to hold the hand-held transducer apparatus continuously or intermittently over the eyeball area of the patient.

A need exists for a non-invasive apparatus and method for monitoring ICP that can be used in emergency, combat or patient transport scenarios by anyone having a small amount of training and that allows intermittent and continuous monitoring without the need for a human user to manually hold the ultrasound transducers.

SUMMARY OF THE INVENTION

In a first aspect of the invention, an apparatus for monitoring Intracranial Pressure (ICP) of a patient includes a wearable device configured for temporary placement on an exterior of a patient's closed eyelid. The wearable device may include a flexible waterproof strip that is conformable to a curvature of the exterior of the patient's closed eyelid. At least two ultrasonic transducer arrays may be fixed on a side of the flexible waterproof strip that faces the patient's closed eyelid. The at least two ultrasonic transducer arrays are separated by a distance on the flexible waterproof strip and arranged to focus on an eyeball area of the patient at an optic nerve. Hydrogel covers the at least two ultrasonic transducer arrays on the flexible waterproof strip. An adhesive adheres the flexible waterproof strip to the patient's closed eyelid.

The apparatus may include a waterproof, conformable, elastic membrane attached to the side of the flexible waterproof strip that faces the patient's closed eyelid. The waterproof, conformable, elastic membrane has the adhesive on an eyelid-facing side to thereby adhere the flexible waterproof strip to the patient's closed eyelid.

The apparatus may include a transceiver located external to the wearable device. The transceiver may be in one of wired and wireless electrical communication with the at least two ultrasound transducer arrays on the flexible waterproof strip. In some embodiments, the transceiver includes a data processor that determines an Optical Nerve Sheath Diameter (ONSD) of the patient from ultrasound images received from the at least two ultrasound transducer arrays. The transceiver may include a visual display that displays the ONSD.

The apparatus may include a power supply disposed on the flexible waterproof strip and in electrical communication with the at least two ultrasonic transducer arrays. The power supply may be one of a single-use battery, a rechargeable battery, and a power supply that receives power via a wire or wirelessly from a source external to the wearable device.

In some embodiments, the transceiver is a portable, hand-held device.

In some embodiments, the wearable device includes at least one flexible circuit board disposed on the flexible waterproof strip and connected to the at least two ultrasound transducer arrays. The at least one flexible circuit board may include a transceiver for data communication and transfer, data processing circuitry, and memory to store ultrasonic image data.

Another aspect of the invention is a method for monitoring Intracranial Pressure (ICP). The method includes providing a wearable device according to the first aspect of the invention and temporarily attaching the wearable device to the patient's closed eyelid. The method includes obtaining ultrasonic images of the patient's optic nerve to produce an image of an optical nerve sheath of the patient and electronically measuring a diameter of the optical nerve sheath.

The method may include visually displaying the diameter on a screen of a mobile transceiver. The ultrasonic images may be obtained intermittently or continuously. The ultrasonic images may be three-dimensional images obtained via triangulation.

The step of providing and temporarily attaching the wearable device may include temporarily attaching the wearable device using an adhesive.

BRIEF DESCRIPTION OF THE DRAWINGS

In the drawings, which are not necessarily to scale, like or corresponding parts are denoted by like or corresponding reference numerals.

DETAILED DESCRIPTION

Figure 1:
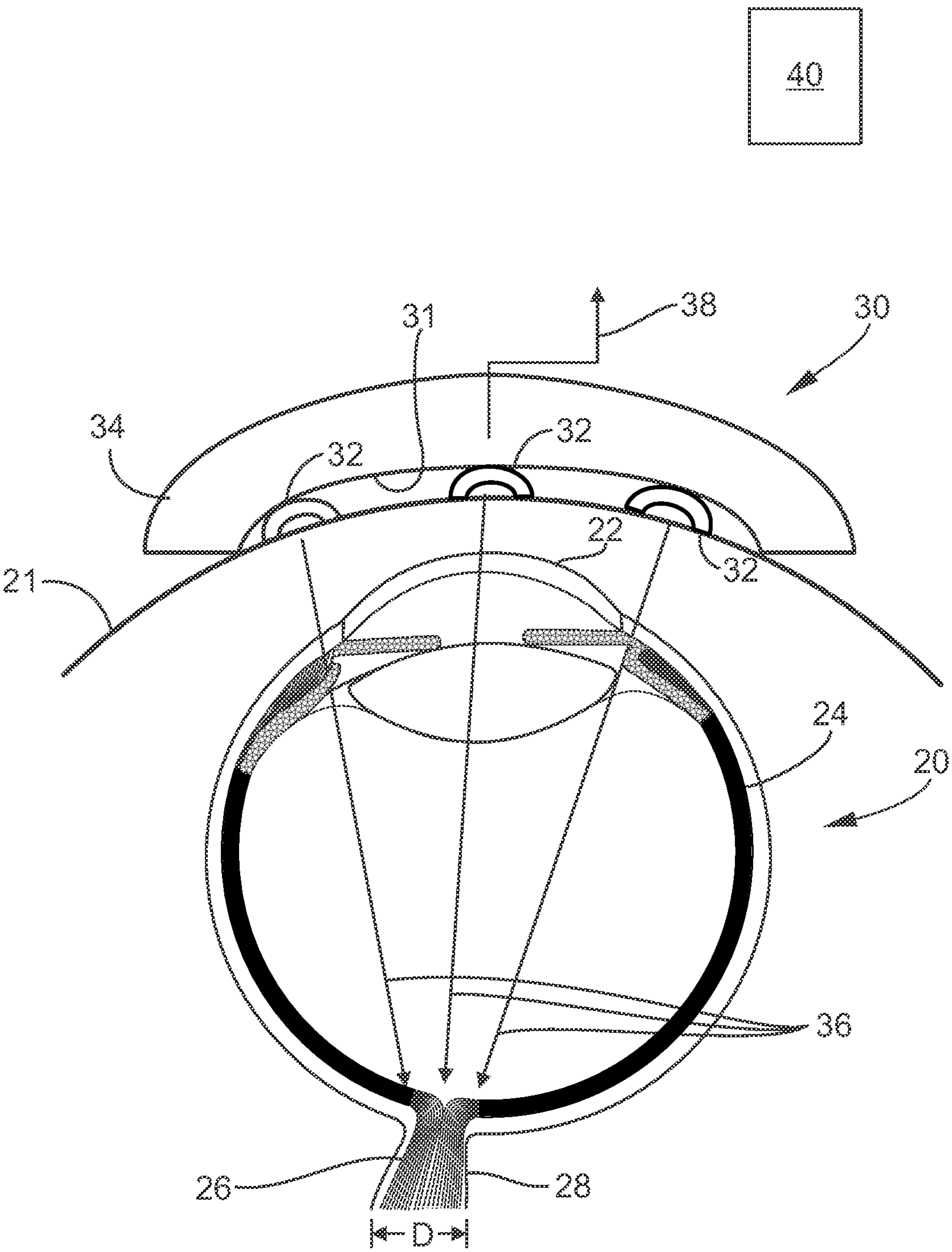
FIG. 1 is a schematic diagram illustrating how one embodiment of the invention works.

The invention includes apparatus and methods for monitoring ICP (Intracranial Pressure). There is a direct correlation between increased ICP and increased ONSD (Optic Nerve Sheath Diameter). One embodiment of the invention is a portable, self-contained, field-use ready device that immediately measures ONSD and enables either intermittent or continuous monitoring of ICP. One embodiment of the novel apparatus includes a non-invasive, wearable device with micro ultrasonic transducer arrays fixed thereon. The wearable device is temporarily attached via an adhesive to the closed eyelid of a conscious or unconscious patient. Using ultrasound sonography, the ultrasonic transducer arrays on the wearable device image the optic nerve behind the eyeball to measure the ONSD. The ONSD provides an indication of the ICP in real time. The usual place to measure ONSD is at a point 3 mm behind the eyeball, although other locations may be used. The wearable device and associated hardware are able to monitor, either intermittently or continuously, in real time, the ICP. The device is a useful monitoring tool to prevent further harm to the patient's brain in certain conditions such as transporting or changing the position of the patient.

The non-invasive wearable device can be placed on a patient's closed eyelid by anyone with simple training and can be applied in the field or in a controlled environment. In addition to military uses, the device can be used by civilian emergency medical units for response, search and rescue and recovery. The device can be used during patient transport and while the patient is in hospital or during evaluation for increased ICP, in both public and private clinics.

The use on the eyelid of a wearable device containing ultrasonic transducers is novel for the measurement of ONSD and monitoring of ICP. The wearable device eliminates the requirement of a skilled technician to hold a device containing ultrasound transducers. In one embodiment, the wearable device may be a pre-packaged, pre-charged, self-contained, lightweight, disposable, battery-powered single use device that wirelessly transmits ultrasound image data to a receiver that is external to the wearable device, for immediate display of the ONSD. Another embodiment is a pre-packaged, lightweight, self-contained wearable device that is rechargeable and may be cleaned and reused on several patients, or for prolonged use on a single patient. Another embodiment is a wearable device that is wired to an external power supply and external data display for longer term monitoring of a patient in transport, in intensive care units or in other medical settings. Some embodiments may receive power wirelessly from an external power supply. Data to and from the wearable device may be transmitted via wire or wirelessly via BLUETOOTH® or other wireless communication to an external transceiver. The data to and from the wearable device may be transmitted to portable devices or traditional visual monitors. Data may also be displayed on a small display disposed on the wearable device. The wearable device may use off-the-shelf medical grade ultrasound transducers and ultrasound imaging circuitry to produce acoustic energy signals that reflect from the back of the eye differentially, thereby enabling measurement of the ONSD. ONSD correlates with ICP and publicly known algorithms can electronically measure ultrasonic images to obtain the ONSD. Some prior art methods use a planar ultrasound transducer array or a fixed curvature ultrasound transducer array in a hand-held device that does not conform to the anatomy of the patient's eyelid and limits the ability to measure the reflected ultrasound signals in three dimensions. Also, the prior art devices are not feasible to use for prolonged monitoring, monitoring in austere environments, or monitoring by inexperienced personnel.

Embodiments of the invention include wearable arrays of ultrasonic transducers separated by a distance to produce a high resolution, triangulated, three-dimensional image of the optic nerve. The wearable device is small enough to fit on the eyelid and may be used with little or no medical training.

FIG. 1 is a schematic diagram illustrating how an embodiment of the invention works to monitor the ICP of a patient. The patient has an eyeball 20 with an eyelid 21, cornea 22, retina 24, optic nerve 26 and optical nerve sheath 28. Sheath 28 has a diameter D. The wearable device 30 includes a waterproof, flexible strip 34 with at least two ultrasonic transducer arrays 32 separated by a distance and fixed on the strip 34. The ultrasonic transducer arrays 32 are covered in a suitable ultrasound gel that is in contact with the exterior of the closed eyelid 21. Device 30 may be placed horizontally, vertically or angularly across the closed eyelid 21. More than two transducer arrays 32 may be used. The transducer arrays 32 transmit ultrasonic sound waves 36 to the area at the rear of eyeball 20 and receives the returned ultrasound waves to obtain images of the optic nerve 26 and sheath 28. Preferably, the diameter D of the optic nerve sheath 28 is measured at a point 3 mm behind the globe of the eyeball 20. The transducers 32 transform the returned acoustic signals into electrical signals 38 that are transmitted wirelessly or via a wire to a transceiver 40 containing a processor, External transceiver 40 may be a portable, handheld device.

The transceiver 40 includes hardware and software to produce a three-dimensional ultrasound image, preferably via triangulation, of the nerve 26 and sheath 28. From this three-dimensional image the transceiver 40 electronically measures diameter D of the optical nerve sheath 28. The diameter D directly correlates to the ICP in the patient. The transceiver 40 may include a visual display or speaker to provide a visual and/or audio indication of the value of diameter D to the user.

Some of the intensive care and emergency point of care ultrasonography literature use the following cutoffs, as measured inner-edge to inner-edge of the sheath 28, for the upper limit of normal ONSD: up to 4 mm in infants; up to 4.5 mm in children; and up to 5 mm in adults. ONSD measurements above these cutoffs may indicate dangerously high levels of ICP.

Figure 2:
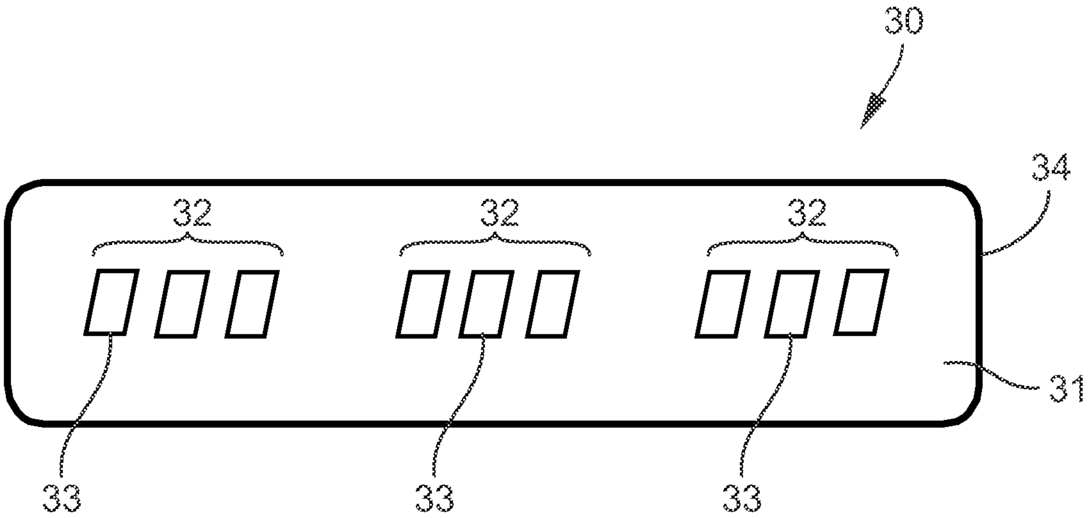
FIG. 2 is a schematic diagram illustrating ultrasonic transducer arrays on the anterior side (facing the eyelid) of the wearable device.
Figure 3:
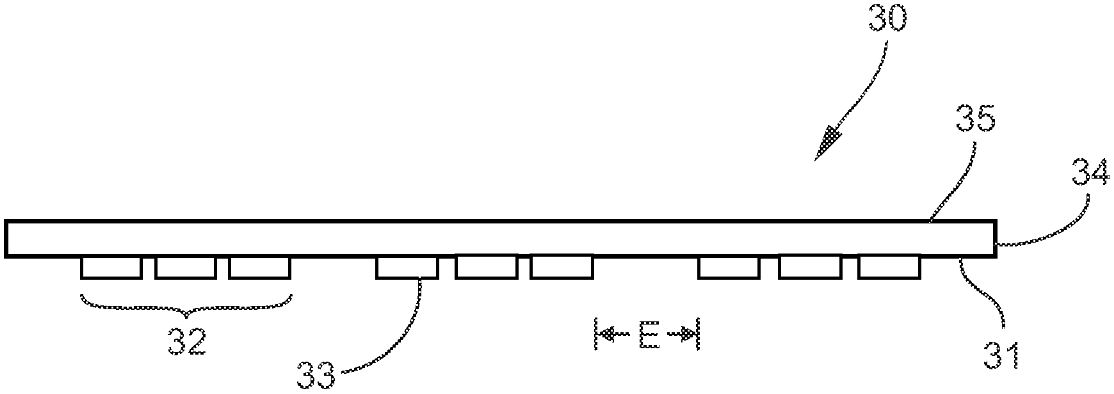
FIG. 3 is a side view of FIG. 2 showing the waterproof, flexible outer layer with the ultrasonic transducer arrays on the eyelid side of the device.

FIG. 2 is a schematic diagram illustrating three ultrasonic transducer arrays 32 on the eyelid contacting side 31 of the wearable device 30. FIG. 3 is a side view of FIG. 2 showing the waterproof, flexible outer layer or side 35. In this embodiment, each transducer array 32 includes three cells 33 although fewer or more cells may be used. Each array 32 is separated a distance from the adjacent array 32, for example, by a distance E. The distances between arrays 32 need not be the same.

Figure 4:
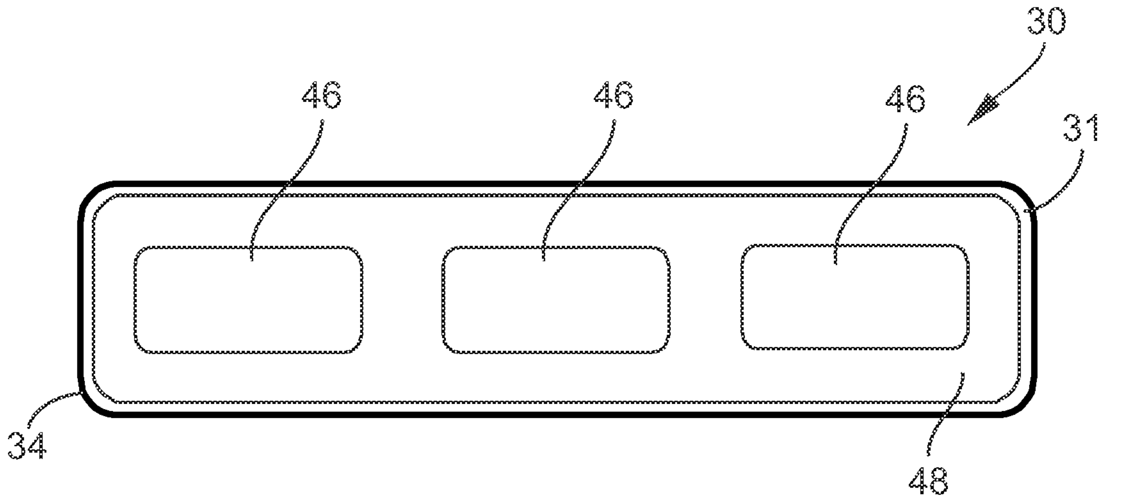
FIG. 4. is a schematic view of the eyelid contacting side of the device showing the transducer arrays covered with hydrogel and each transducer array surrounded by an adhesive.
Figure 5:
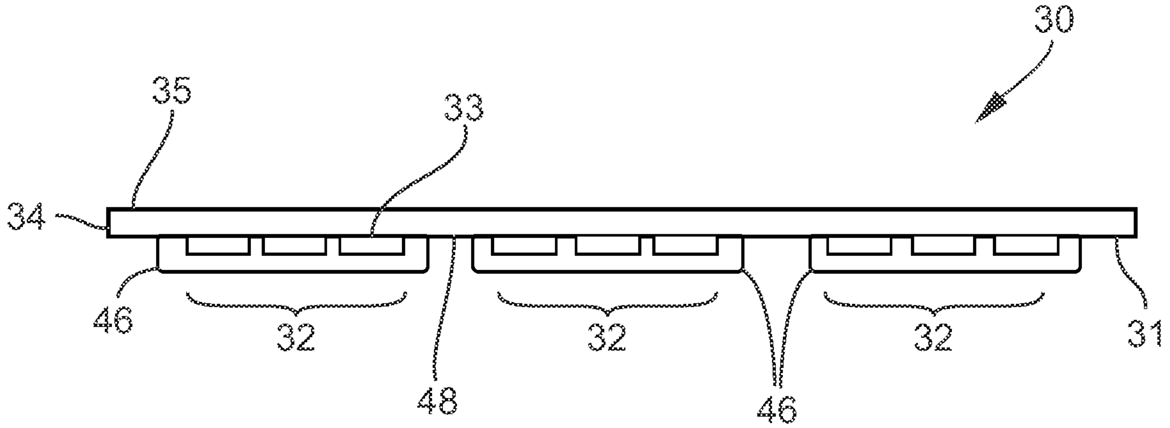
FIG. 5 is a side view of FIG. 4.

FIG. 4 is a schematic view of the wearable device 30 showing the eyelid contacting side 31. FIG. 5 is a side view of FIG. 4. The ultrasonic transducer arrays 32 are covered with hydrogel 46 for signal promotion to and from the optic nerve 26. The arrays 32 are surrounded by an adhesive 48 applied to the side 31 of the strip 34 to temporarily fix the wearable device 30 to the exterior of the closed eyelid 21.

Figure 6:
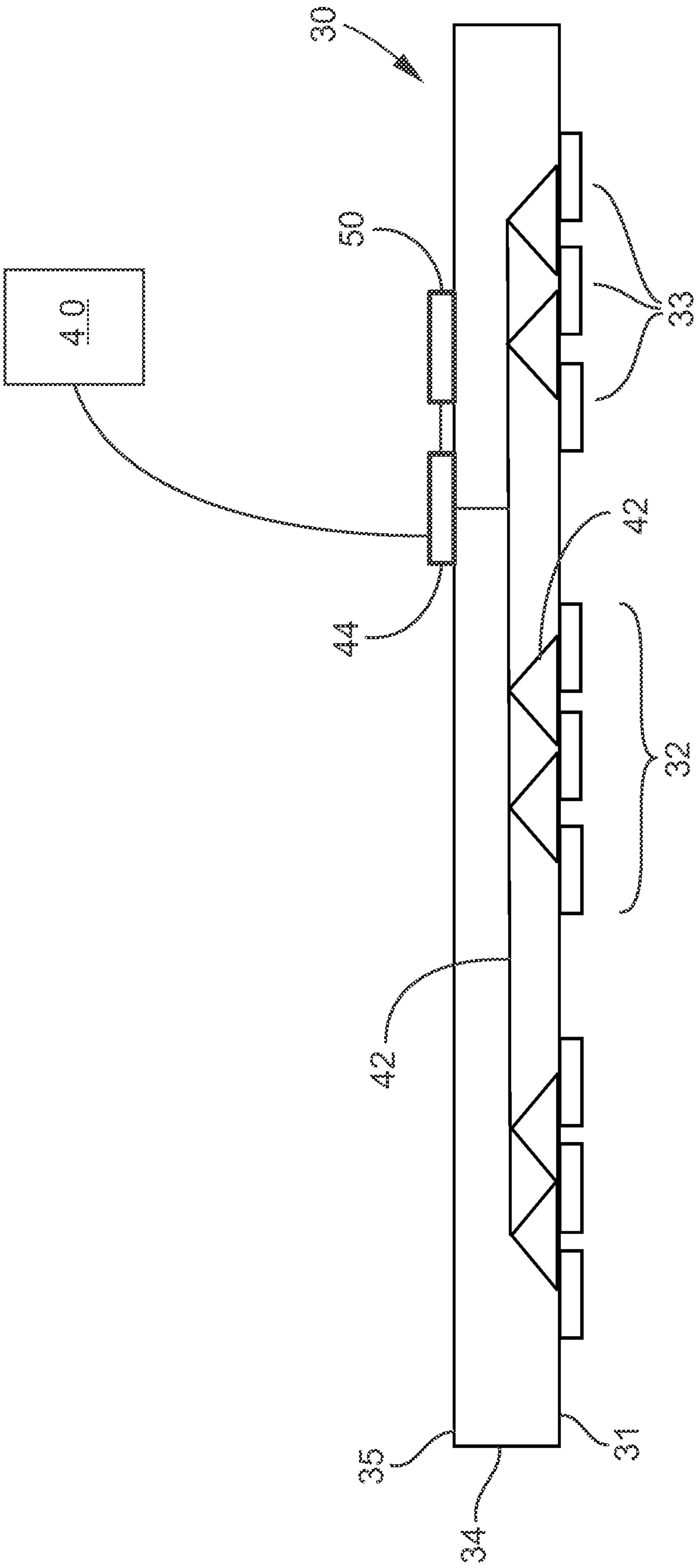
FIG. 6 is a schematic side view of the wearable device showing the ultrasonic transducer arrays wired together.

FIG. 6 is a schematic side view of the wearable device 30 showing the ultrasonic transducer arrays 32 connected with, for example, electrical conductors 42. The arrays 32 may be connected to a transceiver 44 located on the outer side 35 of the flexible strip 34. Transceiver 44 is connected to a power supply 50 located on the outer side 35. Power supply 50 may be pre-charged, for example, power supply 50 may be a pre-charged battery. In other embodiments, power supply 50 may be rechargeable or may be wired to an external power supply, such as an alternating current electrical outlet. External transceiver 40 may be connected via wire 42 or wirelessly to transceiver 44 to transmit data to and from transceiver 44 and power to transceiver 44 and/or power supply 50.

Figure 7:
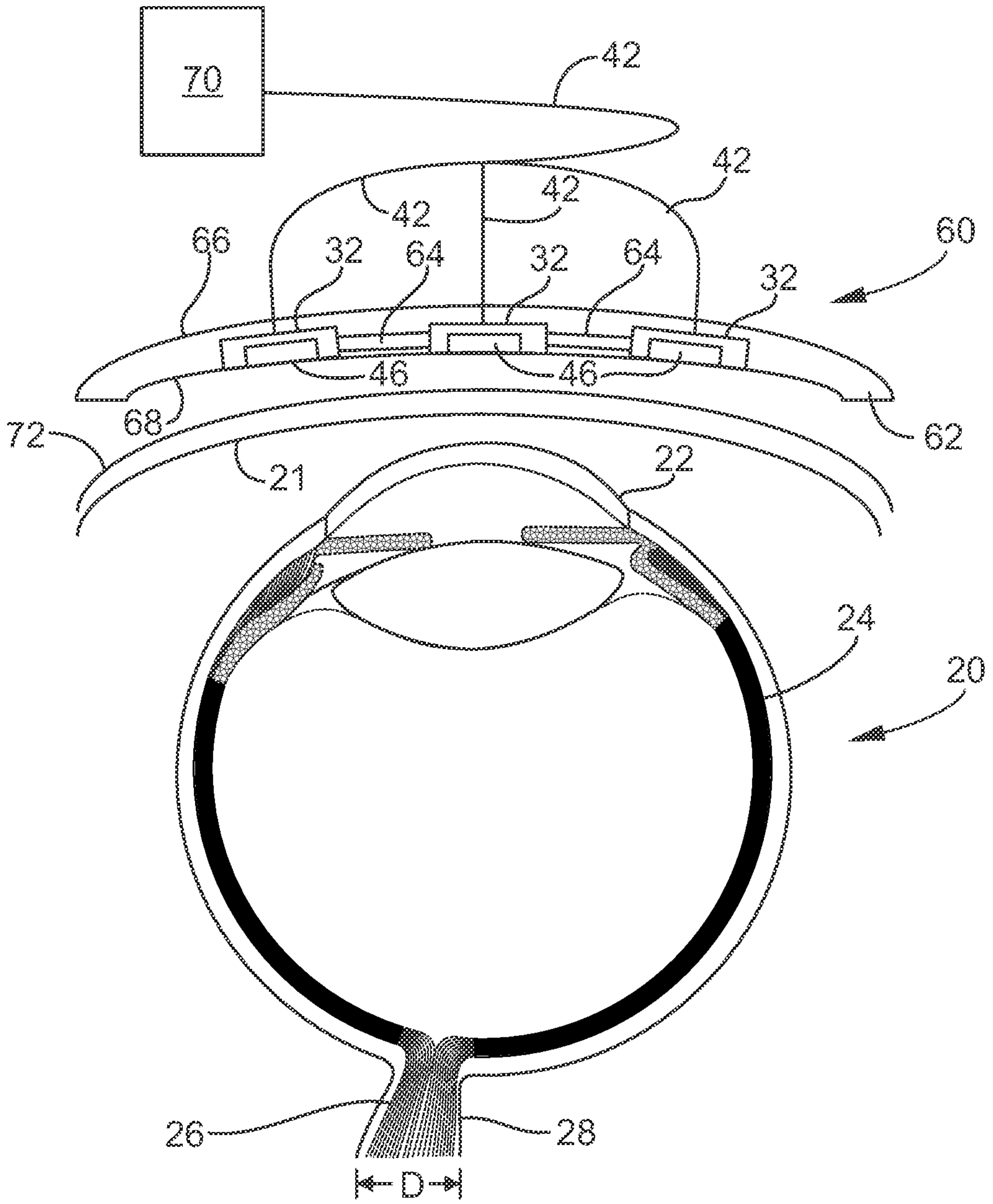
FIG. 7 is a schematic side view of another embodiment of the invention.

FIG. 7 is a schematic side view of another embodiment of the invention. A wearable device 60 has a flexible adhesive strip 62 that holds at least two transducer arrays 32, one or more flexible circuit boards 64, and ultrasound gel 46. The flexible strip 62 enables the transducer arrays 32 to conform to the unique curvature of the eyelid 21 of a patient, thereby improving the ability to acquire three dimensional images. The flexible circuit boards 64 may include microcircuitry for the ultrasound transducers 32, transceiver circuits for data communication and transfer, digital signal processing circuitry, and memory to store image data.

In one embodiment, the flexible circuit boards 64 may include milled slots that hold the ultrasound transducer arrays 32 and the gel 46. The slots may have openings for wiring. Gel 46 is ultrasonic conductive gel or any other medium with suitable acoustic transparency characteristics. The gel 46 may be contained in place on the ultrasound transducers by a thin, waterproof, conformable, elastic membrane 72 having an adhesive on the eyelid-facing side. Membrane 72 may be, for example, OPSITE®. The membrane 72 also keeps the eyelid 21 closed, which is necessary to obtain ultrasound images of the back of the eye through the eyelid 21. In some embodiments, the membrane 72 may be permanently fixed to the wearable device 60. In other embodiments, the membrane 72 facing the ultrasound arrays 32 may be peeled off, thereby enabling reuse of the wearable device 60 by attaching a new membrane 72 that includes hydrogel 46 for the ultrasound sensors and, on the eyelid-facing side of the membrane 72, an adhesive for attachment to the eyelid 21. The side of the membrane 72 that faces the eyelid 21 may include a removable backing that is removed to expose standard medical grade adhesive for attaching the wearable device 60 to the closed eyelid 21.

The ultrasonic arrays 32 may be driven simultaneously or sequentially to improve the quality of the signals. Wires 42 may exit from side 66 of wearable device 60 for connection to external components, such as an external power supply, an external data processor, and/or an external display. Some or all of the external components may be part of a transceiver 70. External transceiver 70 may be a portable, hand-held device. Or, wearable device 60 may be connected wirelessly to an external power supply, an external data processor, and/or an external display, all of which may be part of transceiver 70. Power supplies, data processors and display devices located external to wearable device 60 diminish the small weight the wearable device applies to the eyelid 21. In some embodiments, one or more of a power supply, signal processor and a display device may be placed on the side 66 of the device 60 opposite the eyelid 21.

Any suitable ultrasound transducers may be used to construct the arrays 32, including piezoelectric micromachined ultrasonic elements and capacitive micromachined ultrasonic elements. Brightness mode ultrasound data may be utilized in some embodiments or amplitude mode scanning data may be utilized in other embodiments. The ultrasound transducer arrays 32 preferably triangulate the ultrasound onto the back of the eye, including the optic nerve 26, and enable either a planar or three-dimensional reconstruction of the returned ultrasound energy for immediate, intermittent and continuous monitoring of ICP via ONSD electronic measurement. Data processors may be located on the flexible circuit boards 64 or in the external transceiver 70 to process the image data. The data processors may be used with known machine learning algorithms or later-developed algorithms to target the optic disk for measurement, as well as perform predictive analytics based on the returned data.

As noted above, the wearable device 60 may be connected to an external device, such as a transceiver 70, either with a wire 42 or wirelessly. Either mode of connection can be used to transmit data and/or power. Micro-accelerometers may be attached to the flexible circuit boards 64 to monitor head elevation status during ONSD measurement, as well as to detect if the device 60 has changed position unexpectedly. The ultrasound transducer arrays 32 may be permanently fixed to the thin, lightweight, flexible, water-proof, adhesive backing strip 62 with the arrays 32 standing off the surface of the strip 62 on the anterior side (eyeball facing side) 68. The wearable device 60 is advantageous for emergency situations, including combat casualty care and especially for multidomain medical operations, because of its ability to non-invasively monitor the ICP, either continuously or intermittently, of head injured casualties for both triage and on-going management of head injuries. The wearable device 60 can also be used to assess whether interventions such as elevation of head of the bed, hyperventilation, mannitol and/or hypertonic saline are effective in decreasing ICP of patients. The wearable device 60 can further assist in determining whether a casualty needs a burr hole or decompressive craniectomy. The continuous data provided by the wearable device 60 will allow predictive analytics useful for triage, treatment decisions, and monitoring of these casualties during evacuation.

Some improvements of the invention include its small size, portability, self-containment, ease of use with minimal instruction, non-invasiveness, and useability for emergency, combat, evacuation, transport and hospital environments. Importantly, the need for a person to hold the ultrasonic transducers is eliminated.

Embodiments of the invention have been described to explain the nature of the invention. Those skilled in the art may make changes in the details, materials, steps and arrangement of the described embodiments within the principle and scope of the invention, as expressed in the appended claims.

What is claimed is:

1. An apparatus for monitoring Intracranial Pressure (ICP) of a patient, comprising:
- a wearable device configured for temporary placement on an exterior of a patient's closed eyelid, the wearable device including
- a flexible waterproof strip that is conformable to a curvature of the exterior of the patient's closed eyelid;
- at least two ultrasonic transducer arrays fixed on a side of the flexible waterproof strip that faces the patient's closed eyelid, the at least two ultrasonic transducer arrays separated by a distance on the flexible waterproof strip and arranged to focus on an eyeball area of the patient at an optic nerve;
- hydrogel that covers each of the at least two ultrasonic transducer arrays on the flexible waterproof strip; and
- a waterproof, conformable, elastic membrane attached to the side of the flexible waterproof strip that faces the patient's closed eyelid,
- which the waterproof, conformable, elastic membrane has an adhesive on an eyelid-facing side to thereby temporarily adhere the flexible waterproof strip to the patient's closed eyelid.

2. The apparatus of claim 1, further comprising a transceiver located external to the wearable device, the transceiver being in at least one of wired and wireless electrical communication with the at least two ultrasound transducer arrays on the flexible waterproof strip.

3. The apparatus of claim 2, wherein the transceiver includes a data processor that determines an Optical Nerve Sheath Diameter (ONSD) of the patient from ultrasound images received from the at least two ultrasound transducer arrays.

4. The apparatus of claim 3, wherein the transceiver includes a visual display that displays the ONSD.

5. The apparatus of claim 3, wherein the ONSD is measured at a point 3 mm behind the eyeball area of the patient.

6. The apparatus of claim 2, wherein the transceiver is a portable, hand-held device.

7. The apparatus of claim 1, further comprising a power supply disposed on the flexible waterproof strip and in electrical communication with the at least two ultrasonic transducer arrays.

8. The apparatus of claim 7, wherein the power supply is at least one of a single-use battery, a rechargeable battery, and a power device that receives power via a wire or wirelessly from a source external to the wearable device.

9. The apparatus of claim 1, wherein the wearable device includes at least one flexible circuit board disposed on the flexible waterproof strip and connected to the at least two ultrasound transducer arrays.

10. The apparatus of claim 9, wherein the at least one flexible circuit board includes a transceiver for data communication and transfer, data processing circuitry, and memory to store ultrasonic image data.

11. An apparatus for monitoring Intracranial Pressure (ICP) of a patient, comprising:
- a wearable device configured for temporary placement on an exterior of a patient's closed eyelid, the wearable device including
- a flexible waterproof strip that is conformable to a curvature of the exterior of the patient's closed eyelid;
- at least two ultrasonic transducer arrays fixed on a side of the flexible waterproof strip that faces the patient's closed eyelid, the at least two ultrasonic transducer arrays separated by a distance on the flexible waterproof strip and arranged to focus on an eyeball area of the patient at an optic nerve;
- hydrogel that covers each of the at least two ultrasonic transducer arrays on the flexible waterproof strip; and
- an adhesive that adheres the flexible waterproof strip to the patient's closed eyelid;
- a waterproof, conformable, elastic membrane attached to the side of the flexible waterproof strip that faces the patient's closed eyelid, wherein the waterproof, conformable, elastic membrane has the adhesive on an eyelid-facing side to temporarily thereby adhere the flexiblewaterproof strip to the patient's closed eyelid; and
- a transceiver located external to the wearable device, the transceiver being in at least one of wired and wireless electrical communication with the at least two ultrasound transducer arrays on the flexible waterproof strip.

12. A method for monitoring Intracranial Pressure (ICP), comprising:
- providing the apparatus of claim 1 and temporarily attaching it to the patient's closed eyelid;
- obtaining ultrasonic images of the patient's optic nerve to produce an image of an optical nerve sheath of the patient; and
- electronically measuring a diameter of the optical nerve sheath.

13. The method of claim 12, further comprising visually displaying the diameter on a screen of a mobile transceiver.

14. The method of claim 12, wherein the diameter is measured at a point 3 mm behind the eyeball area of the patient.

15. The method of claim 12, wherein the ultrasonic images are obtained intermittently.

16. The method of claim 12, wherein the ultrasonic images are obtained continuously.

17. The method of claim 12, wherein the ultrasonic images are three-dimensional images obtained via triangulation.

18. The method of claim 12, wherein the step of providing and temporarily attaching includes temporarily attaching using an adhesive.

19. An apparatus for monitoring Intracranial Pressure (ICP) of a patient, comprising:
- a wearable device configured for temporary placement on an exterior of a patient's closed eyelid, the wearable device including
- a flexible waterproof strip that is conformable to a curvature of the exterior of the patient's closed eyelid;
- at least two ultrasonic transducer arrays fixed on a side of the flexible waterproof strip that faces the patient's closed eyelid, the at least two ultrasonic transducer arrays separated by a distance on the flexible waterproof strip and arranged to focus on an eyeball area of the patient at an optic nerve;

a waterproof, conformable, elastic membrane attached to the side of the flexible waterproof strip that faces the patient's closed eyelid with a first adhesive side, wherein the waterproof, conformable, elastic membrane has a second adhesive side on an eyelid-facing side to thereby temporarily adhere the flexible waterproof strip to the patient's closed eyelid, and wherein the elastic membrane is configured to keep the patient's eyelid closed; and hydrogel that covers each of the at least two ultrasonic transducer arrays on the flexible waterproof strip, wherein the hydrogel is contained in place on the ultrasound transducers by the elastic membrane.

* * * * *